US00PP24500P2

(12) United States Plant Patent
Mak

(10) Patent No.: US PP24,500 P2
(45) Date of Patent: May 27, 2014

(54) LILY PLANT NAMED 'TINY ROCKET'

(50) Latin Name: *Lilium hybrida*
Varietal Denomination: Tiny Rocket

(75) Inventor: Niels Johannes Cornelis Mak, Wieringerwerf (NL)

(73) Assignee: Mak 't Zand B.V., 't Zand (NL)

( * ) Notice: Subject to any disclaimer, the term of this patent is extended or adjusted under 35 U.S.C. 154(b) by 81 days.

(21) Appl. No.: 13/507,522

(22) Filed: Jul. 5, 2012

(51) Int. Cl.
*A01H 5/00* (2006.01)

(52) U.S. Cl.
USPC ..... Plt./315; Plt./313

(58) Field of Classification Search
USPC ..... Plt./313, 315
See application file for complete search history.

(56) References Cited

PUBLICATIONS

UPOV-PLUTO Plant Variety Database, 201303, citation for 'Tiny Rocket'.*

* cited by examiner

*Primary Examiner* — Susan McCormick Ewoldt
(74) *Attorney, Agent, or Firm* — C. A. Whealy

(57) ABSTRACT

A new and distinct cultivar of Lily plant named 'Tiny Rocket', characterized by its compact and upright plant habit; vigorous growth habit; densely-foliated habit; freely flowering habit; upright flower buds and flowers; dark greyed purple to greyed red-colored flowers; and good postproduction longevity.

1 Drawing Sheet

Botanical designation: *Lilium hybrida.*
Cultivar denomination: 'TINY ROCKET'.

BACKGROUND OF THE INVENTION

The present Invention relates to a new and distinct cultivar of Lily plant, commercially known as Oriental Hybrid Lily, botanically known as *Lilium hybrida* and hereinafter referred to by the name 'Tiny Rocket'.

The new Oriental Hybrid Lily plant is a product of a planned breeding program conducted by the Inventor in 't Zand, The Netherlands. The objective of the breeding program is to develop new potted Oriental Hybrid Lily plants with erect flowers, attractive flower coloration and good postproduction longevity.

The new Oriental Hybrid Lily plant originated from a cross-pollination in 2001 of two different unnamed proprietary seedling selections of *Lilium hybrida*, not patented. The new Oriental Hybrid Lily plant was discovered and selected by the Inventor as a single flowering plant from within the resultant progeny of the cross-pollination in a controlled greenhouse environment in 't Zand, The Netherlands in May, 2004.

Asexual reproduction of the new Oriental Hybrid Lily plant by bulb scales in a controlled greenhouse environment in 't Zand, The Netherlands since November, 2004 has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tiny Rocket'. These characteristics in combination distinguish 'Tiny Rocket' as a new and distinct Oriental Hybrid Lily plant:

1. Compact and upright plant habit.
2. Vigorous growth habit.
3. Densely-foliated habit.
4. Freely flowering habit.
5. Upright flower buds and flowers.
6. Dark greyed purple to greyed red-colored flowers.
7. Good postproduction longevity.

Plants of the new Oriental Hybrid Lily differ primarily from plants of the female parent seedling selection in the following characteristics:

1. Plants of the new Oriental Hybrid Lily have smaller flowers than plants of the female parent seedling selection.
2. Plants of the new Oriental Hybrid Lily are more freely flowering than plants of the female parent seedling selection.
3. Plants of the new Oriental Hybrid Lily and the female parent seedling selection differ slightly in flower color.

Plants of the new Oriental Hybrid Lily differ primarily from plants of the male parent seedling selection in the following characteristics:

1. Plants of the new Oriental Hybrid Lily are more compact than plants of the male parent seedling selection.
2. Plants of the new Oriental Hybrid Lily have smaller leaves than plants of the male parent seedling selection.
3. Plants of the new Oriental Hybrid Lily and the male parent seedling selection differ slightly in flower color.

Plants of the new Oriental Hybrid Lily can be compared to plants of Oriental Hybrid Lily 'Tiny Hope', disclosed in U.S.

Plant Pat. No. 16,239. Plants of the new Oriental Hybrid Lily differ from plants of 'Tiny Hope' in the following characteristics:

1. Plants of the new Oriental Hybrid Lily are more compact than plants of 'Tiny Hope'.
2. Plants of the new Oriental Hybrid Lily have smaller leaves than plants of 'Tiny Hope'.
3. Plants of the new Oriental Hybrid Lily have smaller flowers than plants of 'Tiny Hope'.
4. Plants of the new Oriental Hybrid Lily and 'Tiny Hope' differ slightly in flower color.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant.

The photograph comprises a side perspective view of a typical flowering plant of 'Tiny Rocket'.

DETAILED BOTANICAL DESCRIPTION

The aforementioned photograph and following observations and measurements describe plants that were grown during the spring in ground beds and 15-cm containers in a glass-covered greenhouse in 't Zand, The Netherlands and under cultural conditions typically used in Oriental Hybrid Lily production. During the production of the plants, day temperatures averaged 15° C., night temperatures averaged 18° C. and light levels averaged 6,000 lux. Measurements and numerical values represent averages for typical flowering plants. Plants were 60 days old when the photograph and description were taken. In the following description, color references are made to The Royal Horticultural Society Colour Chart, 2001 Edition, except where general terms of ordinary dictionary significance are used.

Botanical classification: *Lilium hybrida* 'Tiny Rocket'.

Parentage:

*Female, or seed, parent.*—Unnamed proprietary seedling selection of *Lilium hybrida*, not patented.

*Male, or pollen, parent.*—Unnamed proprietary seedling selection of *Lilium hybrida*, not patented.

Plant description:

*Plant form and growth habit.*—Upright flowering plant; single erect flowering stem with a terminal cluster of flowers; compact and dense plant habit; vigorous growth habit.

*Plant height, soil level to top of flowers.*—About 35 cm.

*Plant diameter, or spread.*—About 20 cm.

*Plant circumference.*—About 64 cm.

*Bulbs.*—Diameter: About 10 cm to 20 cm. Texture: Smooth. Color: Close to 155D.

*Flowering stems.*—Diameter: About 8 mm. Internode length: About 2 cm. Strength: Strong. Texture: Smooth, glabrous. Color: Close to 143A.

*Leaves.*—Arrangement and quantity: Alternate; simple; sessile; about 94 leaves develop per plant. Length, upper leaves: About 8.5 cm. Width, upper leaves: About 1.8 cm. Length, lower leaves: About 10.5 cm. Width, lower leaves: About 2.6 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 147A; venation, close to 147A. Developing and fully expanded leaves, lower surface: Close to 146B; venation, close to 146B.

Flower description:

*Flower shape and aspect.*—Flowers umbellate or funnel-shaped; when fully opened, flowers flatten and tepals recurve towards the apex; flower buds face upright and flowers face upright to slightly outwardly.

*Flowering habit.*—Freely flowering habit, large bulbs will produce eight to ten flowers per flowering stem.

*Fragrance.*—Slightly fragrant.

*Natural flowering season.*—Plants flower in June and July in The Netherlands; plants can be flowered year-round in the greenhouse and forced to bloom about 55 days after planting bulbs.

*Postproduction longevity.*—Good postproduction longevity, flowers last about 10 to 14 days on the plant; tepals not persistent; gynoecium persistent.

*Flower buds.*—Length: About 8.5 cm. Diameter: About 3 cm. Circumference: About 9 cm. Shape: Lanceolate. Color: Close to 143A and 180A; sutures, close to 143A.

*Flower size.*—Diameter: About 13 cm. Length (height): About 8 cm.

*Perianth.*—Quantity and arrangement: Six tepals per flower arranged in two whorls; tepals imbricate. Tepal length, inner tepals: About 9 cm. Tepal width, inner tepals: About 5 cm. Tepal length, outer tepals: About 9 cm. Tepal width, outer tepals: About 4 cm. Tepal shape: Lanceolate. Tepal apex: Acute. Tepal margin: Entire. Tepal texture, upper and lower surfaces: Smooth, glabrous. Tepal color: When opening and fully opened, upper surface: Close to 185A; towards the base, close to 183A; spots, close to 187A; color towards the apex becoming closer to 35A with development. When opening and fully opened, lower surface: Close to 46A.

*Pedicels.*—Angle: About 45° to 70° from vertical. Strength: Strong. Length: About 4.5 cm. Diameter: About 5 mm. Texture: Smooth, glabrous. Color: Close to 143B.

*Reproductive organs.*—Stamens: Quantity per flower: Six. Filament length: About 5.8 cm. Filament color: Close to 170D and 179A. Anther length: About 1.4 cm. Anther color: Close to 173B. Pollen color: Close to 172C. Pistils: Quantity per flower: One. Style length: About 4.7 cm. Style color: Close to 170D and 179A. Stigma diameter: About 3 mm. Stigma shape: Lobed. Stigma color: Close to 79A.

*Fruits.*—Length: About 2 cm. Diameter: About 5 mm. Color: Close to 144C.

*Seeds.*—No viable seeds have been observed on plants of the new Oriental Hybrid Lily plant.

Disease & pest resistance: Resistance to pathogens and pests common to Oriental Hybrid Lilies has not been observed on plants of the new Oriental Hybrid Lily.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Tiny Rocket' as illustrated and described.

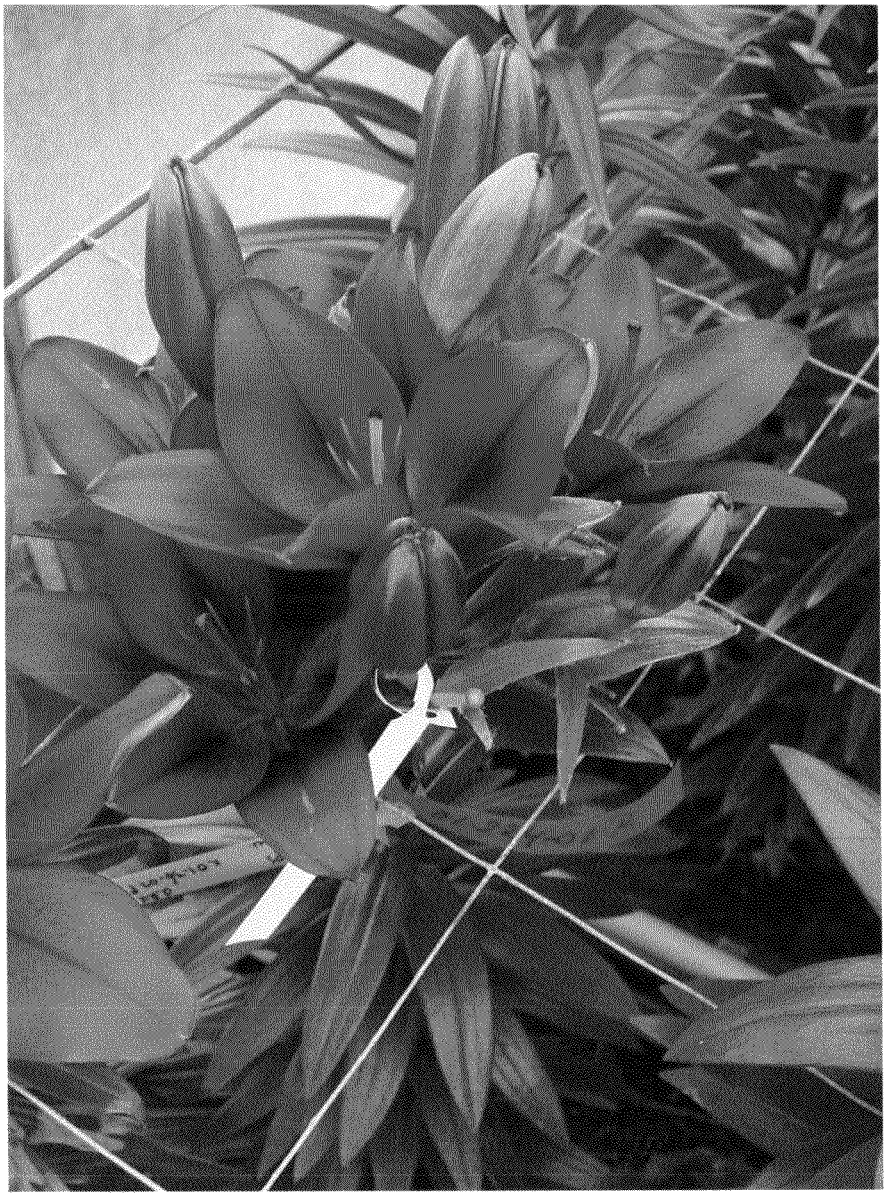

* * * * *